United States Patent
Takahashi (10) Patent No.: US 8,189,888 B2
(45) Date of Patent: May 29, 2012

(54) MEDICAL REPORTING SYSTEM, APPARATUS AND METHOD

(75) Inventor: Noriyuki Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 921 days.

(21) Appl. No.: 12/212,863

(22) Filed: Sep. 18, 2008

(65) Prior Publication Data

US 2009/0087049 A1   Apr. 2, 2009

(30) Foreign Application Priority Data

Sep. 27, 2007  (JP) .................................. 2007-252661

(51) Int. Cl.
 *G06K 9/00* (2006.01)

(52) U.S. Cl. .......................... 382/128; 382/159; 382/305

(58) Field of Classification Search .................. 382/128, 382/159, 305
See application file for complete search history.

(56) References Cited

U.S. PATENT DOCUMENTS

2004/0081342 A1* 4/2004 Sato .............................. 382/128

FOREIGN PATENT DOCUMENTS

JP         2004-305289 A    11/2004

* cited by examiner

*Primary Examiner* — Theresa T Doan
(74) *Attorney, Agent, or Firm* — Sughrue Mion, PLLC (57) ABSTRACT

A medical reporting system includes a display panel for displaying plural CT images. A ROI setting unit designates a region of interest in the CT images. A group setting unit sets a group of specific CT images having the region of interest among the CT images, to generate group information of the group. A report editor displays a note area for inputting a note related to the specific CT images. A memory stores a text location of the note area assigned to the group information, and stores location information of the region of interest in the specific CT images. Furthermore, a first terminal device has the report editor, the ROI setting unit and the group setting unit. A second terminal device communicates with the first terminal device on line. A reporting display panel displays at least the specific CT images and the note.

14 Claims, 9 Drawing Sheets

MEDICAL REPORTING SYSTEM, APPARATUS AND METHOD

BACKGROUND OF THE INVENTION

1. Field of the Invention

The present invention relates to a medical reporting system, apparatus and method. More particularly, the present invention relates to a medical reporting system, apparatus and method in which a set of plural medical images can be handled for observation without error for high precision in the diagnosis.

2. Description Related to the Prior Art

In a hospital as medical facilities, various modality systems are utilized for diagnosis, including a CR (computed radiography) device, CT (computed tomography) device, MRI (magnetic resonance imaging) device, PET (positron emission tomography) device, and ultrasonic diagnosis device. To examine a patient, a doctor utilizes medical images obtained by modality systems to find symptoms of the patient in a precise manner.

The doctor of each of hospital departments requests a diagnostic radiologist as specialized doctor of an inspection department who reads the medical image for the purpose of diagnosis. The radiologist, after reading the medical image in response to the request, writes a medical report and sends it to the doctor of the specific hospital department. Then he or she makes a patient note by final observation of the patient in consideration of the medical report.

A medical image filing system has been recently proposed to raise efficiency in medical management. The medical images and progress notes are processed electronically, so image reading is carried out on line. For example, JP-A 2004-305289 discloses producing the medical report in the medical image filing system. Attribute information is added to a note area in the medical report for determining the medical image and a text location within the medical image. A portion of the medical image assigned with the note can be easily recognized.

In the medical examination, a region of interest of an organ, lesion or site within a body extends in a three dimensional manner. In general, a plurality of medical images are created for examination with the CT or MRI device.

In JP-A 2004-305289, however, manual operation is complicated typically if the region of interest appears in any of a plurality of medical images. The medical images are designated by one image, and the region of interest is designated by one region in the medical image, for the purpose of assignment of the progress note. Furthermore, there is no grouping of images of the region of interest being the same. There is no association of two or more regions of interest in the medical image. After the medical report is edited, there occurs a problem when the doctor wishes to refer to the medical report visually for diagnosis. Every one of the medical images must be observed according to comments in the medical report. There is no simultaneous observation of a plurality of medical images. There is no concentrated observation of the region of interest for a plurality of medical images. Precision in the diagnosis cannot be higher, because of limited efficiency in the observation of the medical images in an electronic manner.

SUMMARY OF THE INVENTION

In view of the foregoing problems, an object of the present invention is to provide a medical reporting system, apparatus and method in which a set of plural medical images can be handled for observation without error for high precision in the diagnosis.

In order to achieve the above and other objects and advantages of this invention, a medical reporting system includes a display panel for displaying plural medical images. A ROI setting unit designates a region of interest in the medical images A group setting unit sets a group of specific medical images having the region of interest among the plural medical images, to generate group information of the group. A report editor displays a note area for inputting a note related to the specific medical images. An assigning unit assigns a text location of the note area to location information of the region of interest in the specific medical images assigned to the group information, so as to store the text location and the location information.

The ROI setting unit extracts an abnormal shadow from data of the medical images, and the region of interest is a portion with the abnormal shadow.

Furthermore, there is a reporting display panel. A display control unit controls the reporting display panel according to the text location and the location information assigned to the group information, to display the specific medical images, the region of interest and the note.

Furthermore, an additional memory stores metadata assigned to the medical images and adapted to discernment. The report editor causes display of the metadata of the specific medical images in the note area among the medical images.

The display control unit displays the specific medical images according to the group information and the location information.

The display control unit enlarges or reduces the specific medical images simultaneously in the reporting display panel by display control.

In one preferred embodiment, the display control unit enlarges or reduces the specific medical images discretely from one another by display control.

Also, the display control unit moves the specific medical images simultaneously in a scroll manner.

In another preferred embodiment, the display control unit moves the specific medical images in a scroll manner discretely from one another by display control.

Furthermore, a first terminal device has the report editor, the ROI setting unit and the group setting unit. A second terminal device communicates with the first terminal device through a network. A reporting display panel is controlled by the second terminal device, for displaying at least the specific medical images and the note.

The plural medical images are tomographic images of a body.

Furthermore, a processor combines the tomographic images to reconstruct a 3D image.

Also, a medical reporting apparatus includes a display panel for displaying plural medical images. A ROI setting unit designates a region of interest in the medical images. A group setting unit sets a group of specific medical images having the region of interest among the plural medical images, to generate group information of the group. A report editor displays a note area for inputting a note related to the specific medical images. A memory stores a text location of the note area assigned to the group information, and for storing location information of the region of interest in the specific medical images assigned to the group information.

Also, a medical reporting method includes a display step of displaying plural medical images. In a ROI setting step, a region of interest in the medical images is designated. In a group setting step, a group of specific medical images having the region of interest is set among the plural medical images, to generate group information of the group. In an editing step, a note area is displayed for inputting a note related to the specific medical images. In an assigning step, a text location of the note area is assigned to the group information, and location information of the region of interest in the specific medical images is assigned to the group information.

In one preferred embodiment, a computer executable program for medical image filing is provided, and includes a display program code for displaying plural medical images. A ROI setting program code is for designating a region of interest in the medical images. A group setting program code is for setting a group of specific medical images having the region of interest among the plural medical images, to generate group information of the group. An editing program code is for displaying a note area for inputting a note related to the specific medical images. An assigning program code is for assigning a text location of the note area to the group information, and assigning location information of the region of interest in the specific medical images to the group information.

Also, a user interface for medical image filing is provided, and includes a screen area for displaying plural medical images. A ROI setting region designates a region of interest in the medical images. A group setting region sets a group of specific medical images having the region of interest among the plural medical images, to generate group information of the group. There is a note area for inputting a note related to the specific medical images. An assigning region assigns a text location of the note area to the group information, and assigning location information of the region of interest in the specific medical images to the group information.

In another preferred embodiment, a medical reporting system includes an image storage for storing information of plural medical images. A ROI memory stores information of a region of interest designated in the medical images. A group information memory stores group information generated by setting a group of specific medical images having the region of interest among the plural medical images. A note area memory stores information of a note area for inputting a note related to the specific medical images. A memory stores a text location of the note area assigned to the group information, and stores location information of the region of interest in the specific medical images.

Consequently, a set of plural medical images can be handled for observation without error for high precision in the diagnosis, because the group information can be checked to verify the specific medical images to be read, and the text location and location of the region of interest are assigned to a group of the specific medical images.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
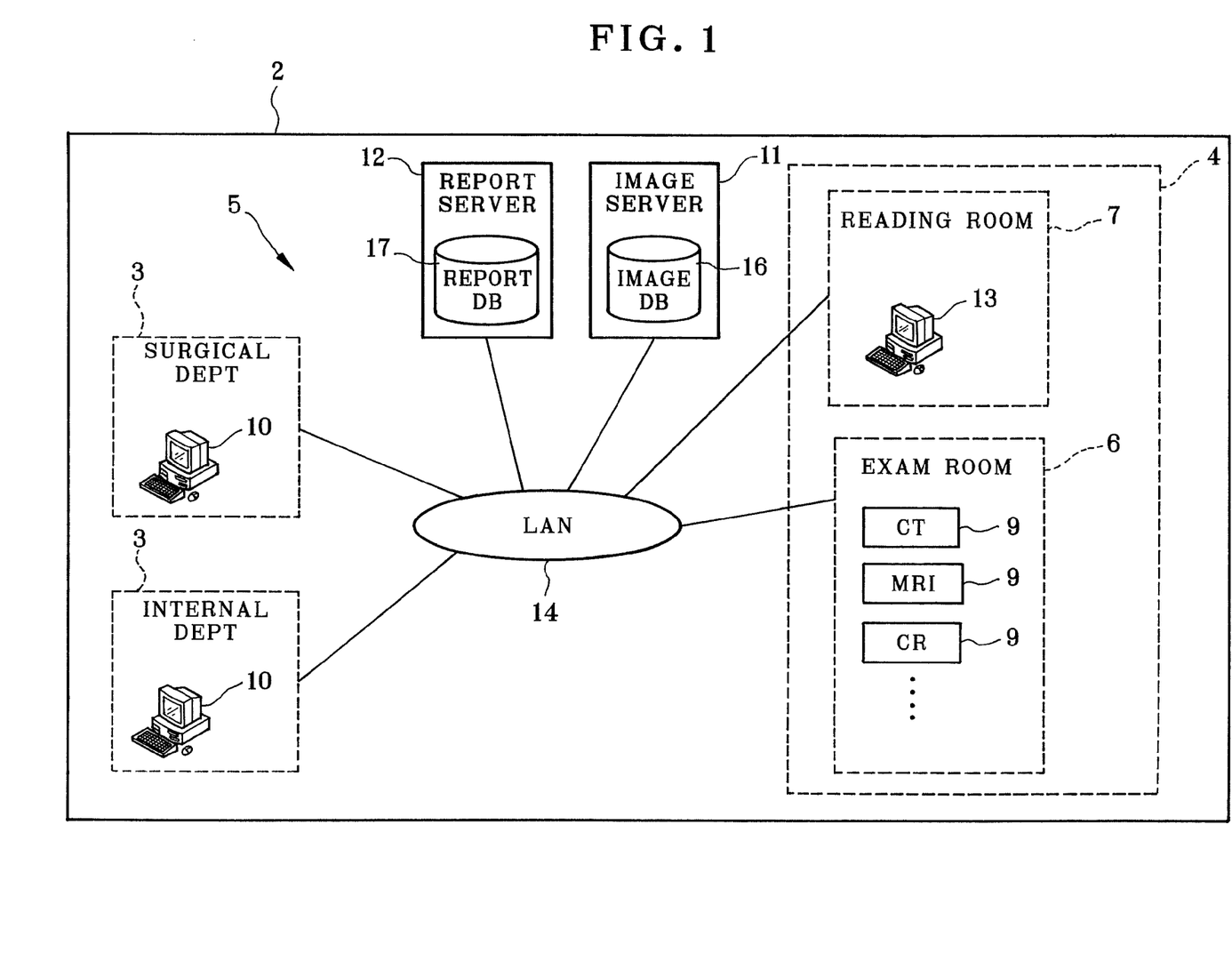
FIG. 1 is a block diagram schematically illustrating a medical reporting system.

In FIG. 1, a hospital 2 of a large scale has specific hospital departments 3, for example, internal, surgical and other departments, an inspection department 4, and a medical reporting system 5 as medical network system for medical image filing. The inspection department 4 has an examination room 6 where a patient's body is examined to obtain medical images, and a reading room 7 where a doctor or radiologist reads medical images. Various modality systems 9 of high precision for medical use are installed in the examination room 6, including CT (computed tomography) device, MRI (magnetic resonance imaging) device, CR (computed radiography) device and the like.

The medical reporting system 5 includes local terminal devices 10, an image server 11, a report server 12, a report editing terminal device 13 for medical image filing, an LAN (local area network) 14 for communication between those devices.

The image server 11 has an image database (DB) 16. The report server 12 has a report database (DB) 17. An example of storage for the image database 16 and the report database 17 is a hard disk drive (HDD). After examination is requested in the inspection department 4, medical images are created by each of the modality systems 9. A case number (inspection ID) is assigned to the medical images from the modality systems 9. Data of the medical images are transmitted through the LAN 14 to the image server 11, and stored to the image database 16. The report database 17 stores information of a report as a data file edited by the report editing terminal device 13. The local terminal devices 10 are installed in the hospital departments 3 on the side of request of examination. A doctor utilizes one of the local terminal devices 10 to request the examination, to display a report, and for various purposes.

Figure 2:
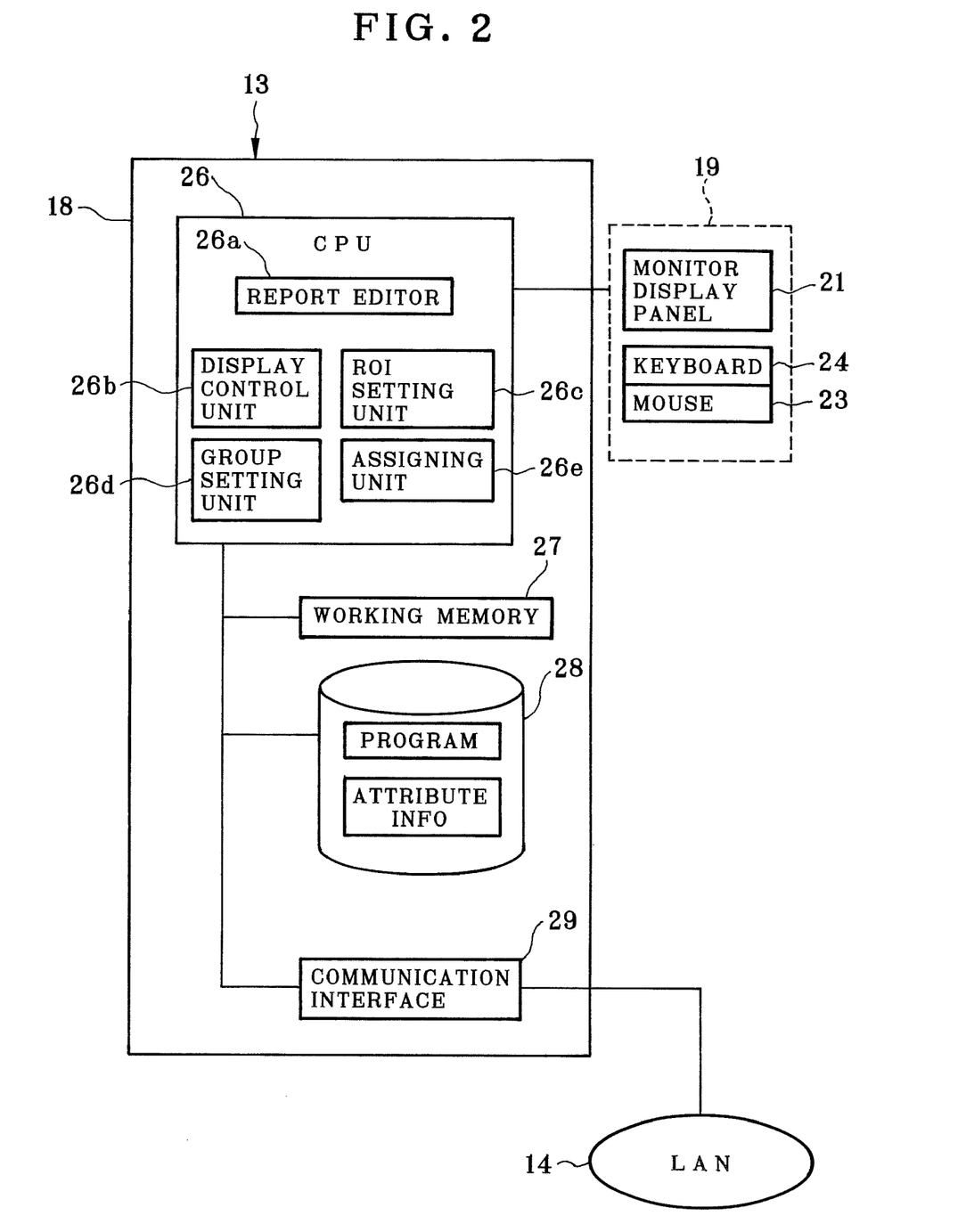
FIG. 2 is a block diagram schematically illustrating a terminal device in the medical reporting system.

The report editing terminal device 13 is installed in the reading room 7, and is constituted by any one of a personal computer, workstation and the like and a computer executable program set up therein for medical image filing. In FIG. 2, the report editing terminal device 13 includes a computer main unit 18 and a service console 19. An input interface in the service console 19 includes a monitor display panel 21, a mouse 23, and a keyboard 24. An editing screen area 30 as user interface for medical image filing appears on the monitor display panel 21 by the control of the report editing terminal device 13 according to transmitted data and other information.

The computer main unit 18 includes a CPU 26, a working memory 27, a hard disk drive (HDD) 28 and a communication interface 29. The hard disk drive 28 is a well-known data storage device, and stores the operating system (OS), various programs, attribute information (inspection information) of medical images, and the like. Examples of the attribute information include information of case number, patient ID, patient's name, modality, inspection condition and the like. The working memory 27 is a temporary memory for use in executing a control program in the monitor display panel 21. The communication interface 29 performs control of communication according to a communication protocol in the LAN 14 for transmitting and receiving data on line.

The CPU 26 controls various elements in the computer main unit 18, and runs a computer executable program to edit a medical report. Thus, the CPU 26 includes elements of a report editor 26a, a display control unit 26b, a ROI setting unit 26c, a group setting unit 26d and an assigning unit 26e.

Figure 3:
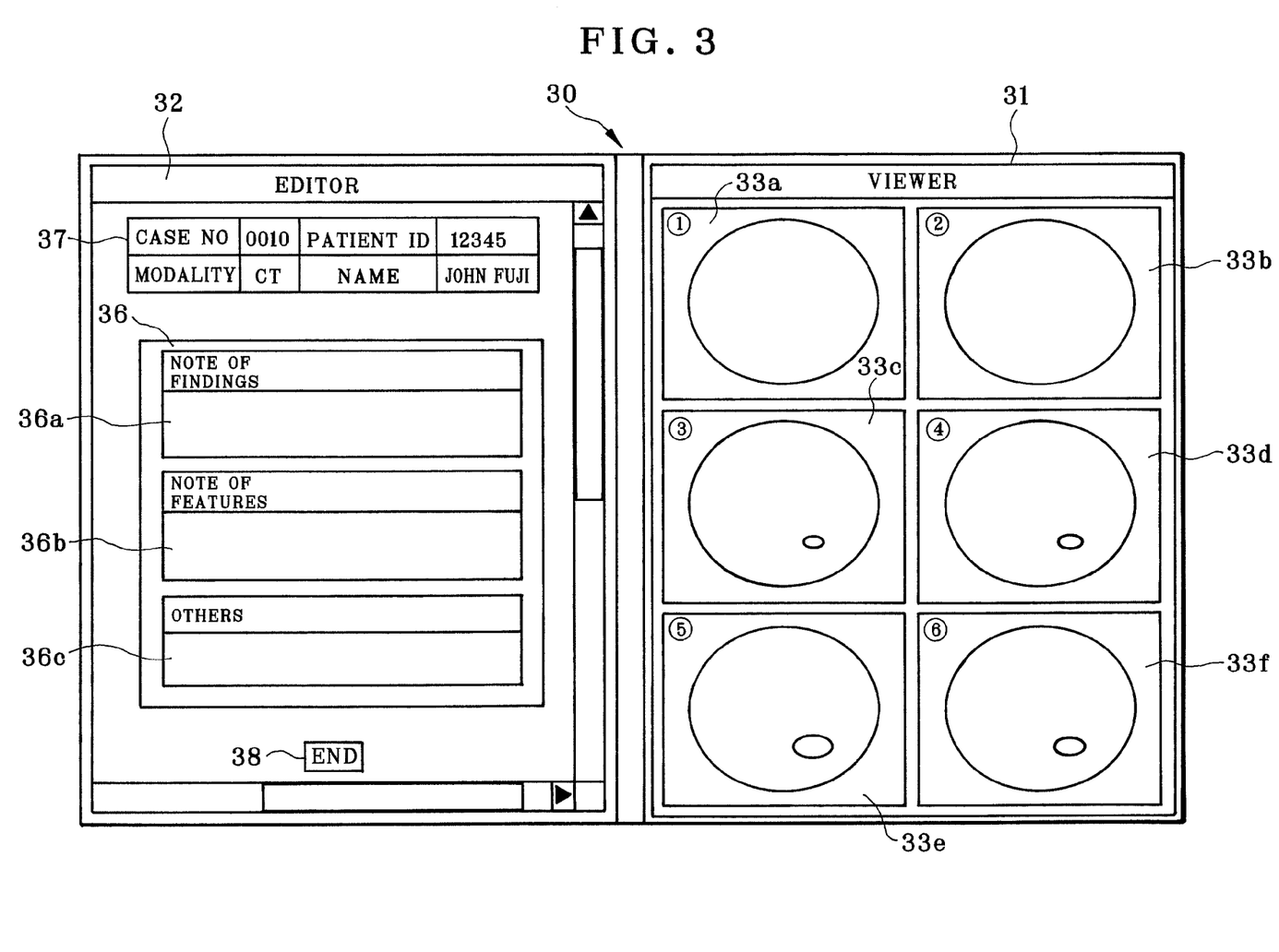
FIG. 3 is a front elevation illustrating an editing screen area.
Figure 6:
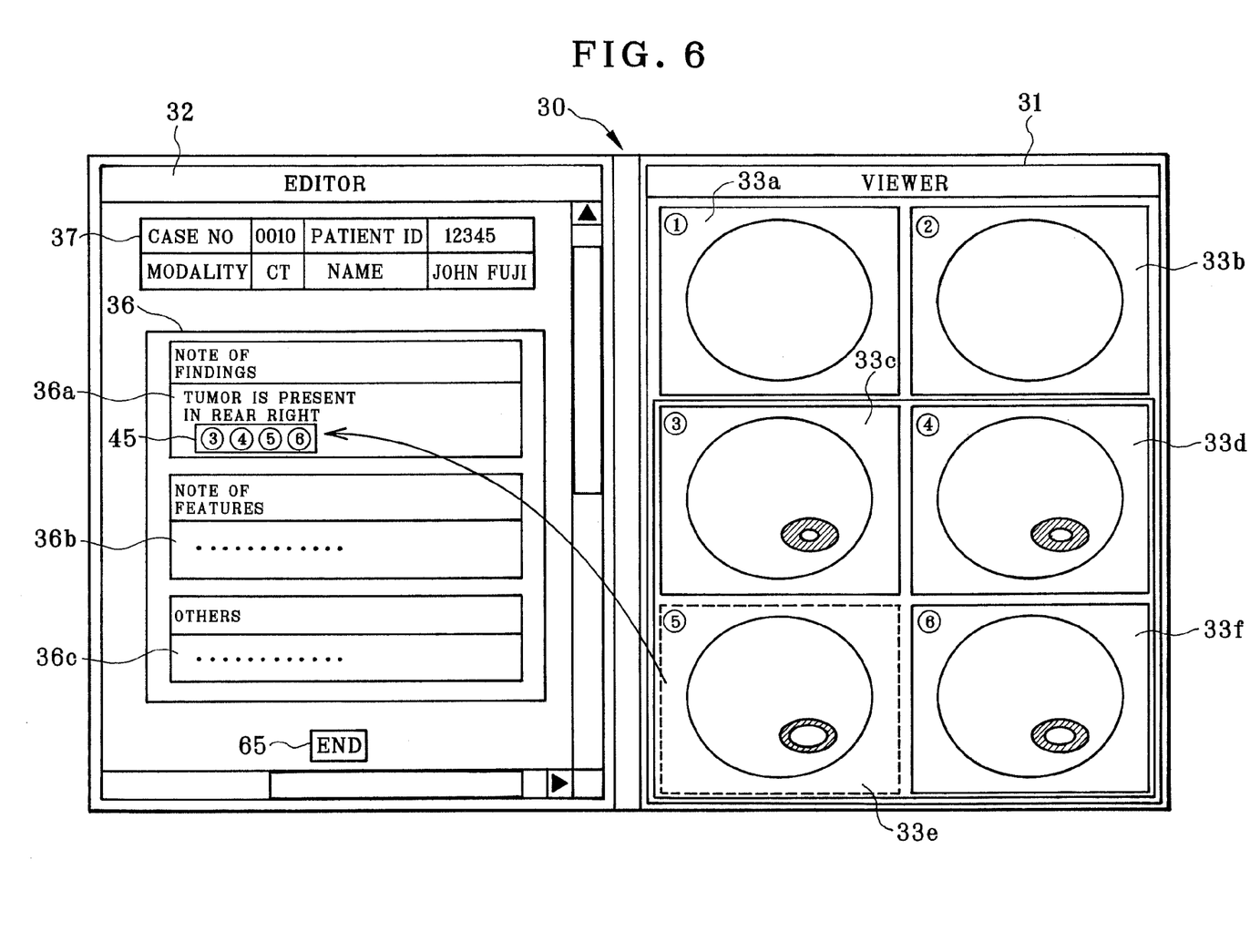
FIG. 6 is a front elevation illustrating a screen area in which information is assigned to a note area.

In FIG. 6, the editing screen area 30 is displayed on the monitor display panel 21, while the display control unit 26b operates. The editing screen area 30 includes a region of a viewer 31 and a region of an editor 32. The region of the viewer 31 displays medical images read from the image database 16. In the examination of the CT, MRI or the like with plural images, all medical images from one time of the examination are displayed together. For example, six CT (computed tomography) images 33a-33f as medical images are created by the CT device and displayed in the region of the viewer 31 at one time. The CT images 33a-33f are obtained by consecutive slice of a patient's body on planes as a cross section. The CT image 33a is assigned with metadata of No. 1 as created in the lowest position among the CT images 33a-33f. The CT images 33b-33f are assigned with metadata of Nos. 2-6, because created one after another upwards from the lowest position.

In the region of the editor 32 are indicated a patient note window 36 for a note or comment, attribute information 37 of the inspection, and a completion button 38. The patient note window 36 has patient note areas 36a, 36b and 36c for a note or comment of findings, features and the like according to observation. When a pointer of a mouse is positioned at each of the patient note areas 36a-36c, a keyboard is manually operated to draft and input a note. For example, a diagnostic radiologist after reading the images inputs a note for the CT image 33a to at least one of the patient note areas 36a-36c. In the embodiment, a note for presence of a lesion in the CT images 33c-33f of Nos. 3-6 is drafted and input to the patient note area 36a as a finding. In response to the input, the assigning unit 26e operates for assigning the information of CT images with a text location of the note.

Figure 4:
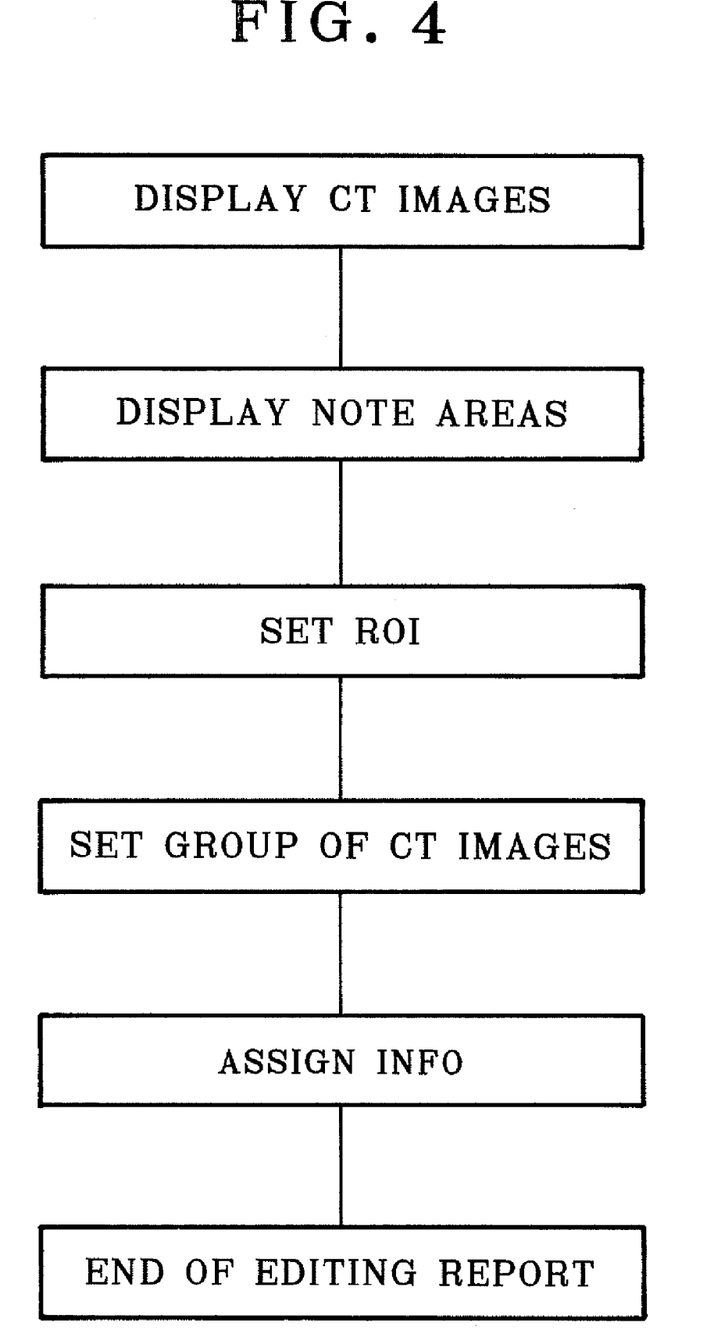
FIG. 4 is a flow chart illustrating a process of editing a medical report.

In FIG. 4, a flow chart is illustrated for a process in the report editing terminal device 13 with steps of inputting a note, assigning image information, and finally editing a report.

To edit a medical report in the report editing terminal device 13, at first the service console 19 is manually operated to input a case number (inspection ID). The image server 11 is accessed to retrieve medical images from the image database 16 according to the case number. Also, attribute information (inspection information) assigned with the case number is read from the hard disk drive 28. The report editing terminal device 13 displays the editing screen area 30 of FIG. 3, so the radiologist creates a medical report by following instructions on the editing screen area 30.

The radiologist after reading the CT images 33a-33f on the region of the viewer 31 drafts and inputs a note at the patient note areas 36a-36c, and then designates a region of interest (ROI) 40 where a lesion is present within each of the CT images 33a-33f. To this end, a service console is operated to enter a signal for the designation. When he or she moves a cursor around a portion of the lesion by clicking the mouse 23, the ROI setting unit 26c operates to designate the region of interest 40 with a slightly larger range than the lesion pointed by a click. The region of interest 40 is indicated in a specific form distinct from the remaining portion of each of the CT images 33a-33f, for example, with a different brightness, with a clear contour line, with a specific color, or in a filtered form.

Note that various known techniques can be used for designating the region of interest (ROI) 40 in medical images, for example, CAD (Computer Aided Diagnosis) system, in which abnormal shadows are automatically extracted from data of medical images, to designate portions of the abnormal shadows as the region of interest 40.

Figure 5A:
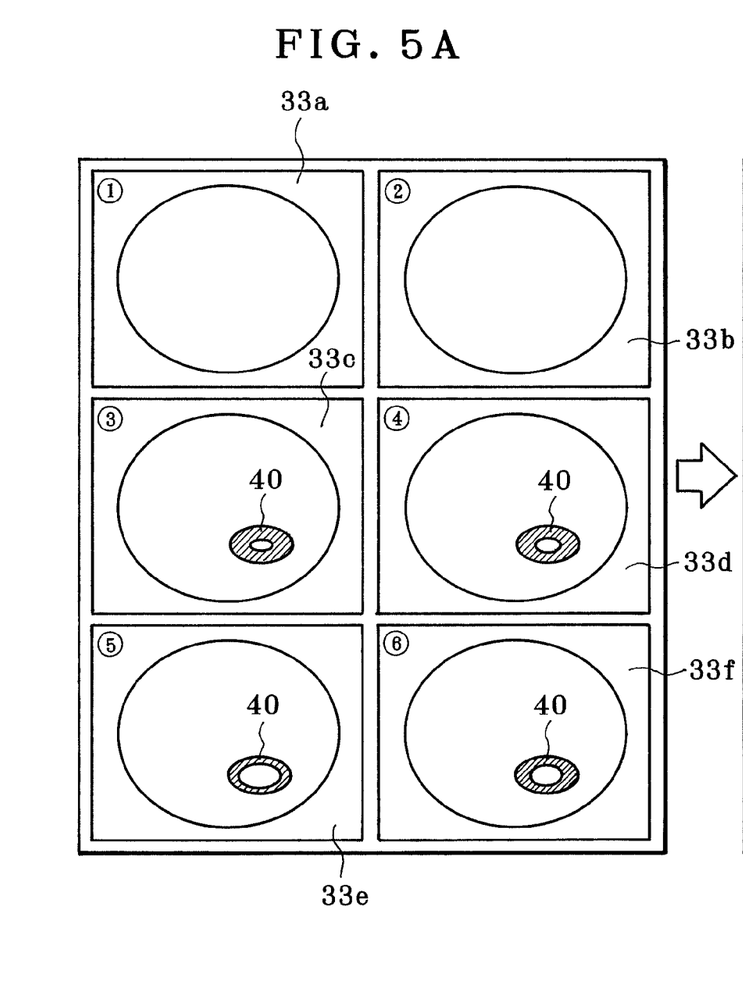
FIG. 5A is a front elevation illustrating a screen area of designating a region of interest.
Figure 5B:
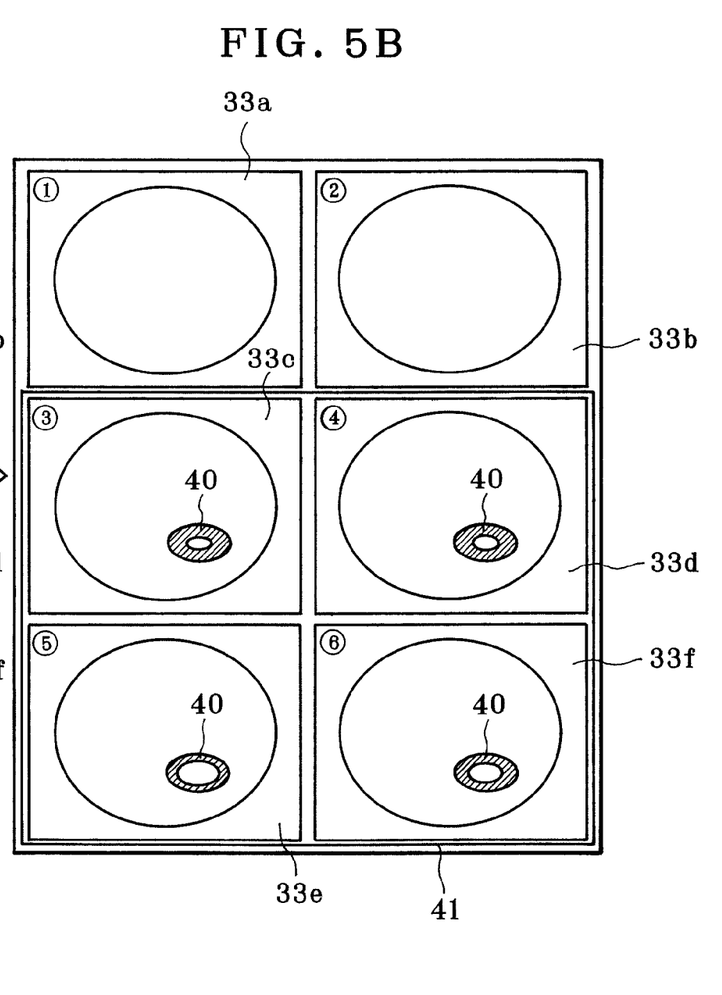
FIG. 5B is a front elevation illustrating a screen area of setting a group of CT images.

For all the CT images 33c-33f of Nos. 3-6, the region of interest (ROI) 40 is designated as illustrated in FIG. 5A. Then the group setting unit 26d selectively designates the CT images 33c-33f after designation of the region of interest 40, to produce group information as illustrated in FIG. 5B. In the embodiment, the group information is defined by a group of the CT images 33c-33f of Nos. 3-6, and is stored in the working memory 27. Note that frame lines 41 appear about CT images for clarifying the group setting of the CT images 33c-33f of Nos. 3-6. The group will correspond to a data file later.

After the group setting, the CT image 33e of No. 5 is selected among the CT images 33c-33f of Nos. 3-6 in the group. The mouse 23 is operated for drag. A pointer of the mouse 23 is set near to the note in the patient note area 36a and is operated for drop. Then the assigning unit 26e designates a text location 45 of the patient note area 36a at the pointer. The text location 45 is stored in association with the group information and information of the position and size of the region of interest (ROI) 40 in the CT images 33c-33f according to the group information. Note that various modes of inputs can be used in place of the drag and drop of the mouse 23, for example, an input of a short-cut key on the keyboard 24 or other predetermined mode with any of input devices. Then Nos. 3-6 of the CT images as metadata are indicated in the text location 45 and near to the note for easy recognition of the assignment in a visual manner.

Then the completion button 38 is clicked upon completion of inputting a note and assignment to the note. The report editor 26a operates in response to the click, to edit a medical report or a data file including the note and meta information assigned to the note. The medical report is stored in the report database 17.

The medical report edited by the report editing terminal device 13 is read from the report database 17, so as to display information of the note and images assigned with the note. In the embodiment, the local terminal device 10 as second terminal device operates to retrieve the medical report in a separate manner from the report editing terminal device 13. However, the report editing terminal device 13 as a single device may edit and then retrieve a medical report.

Figure 7:
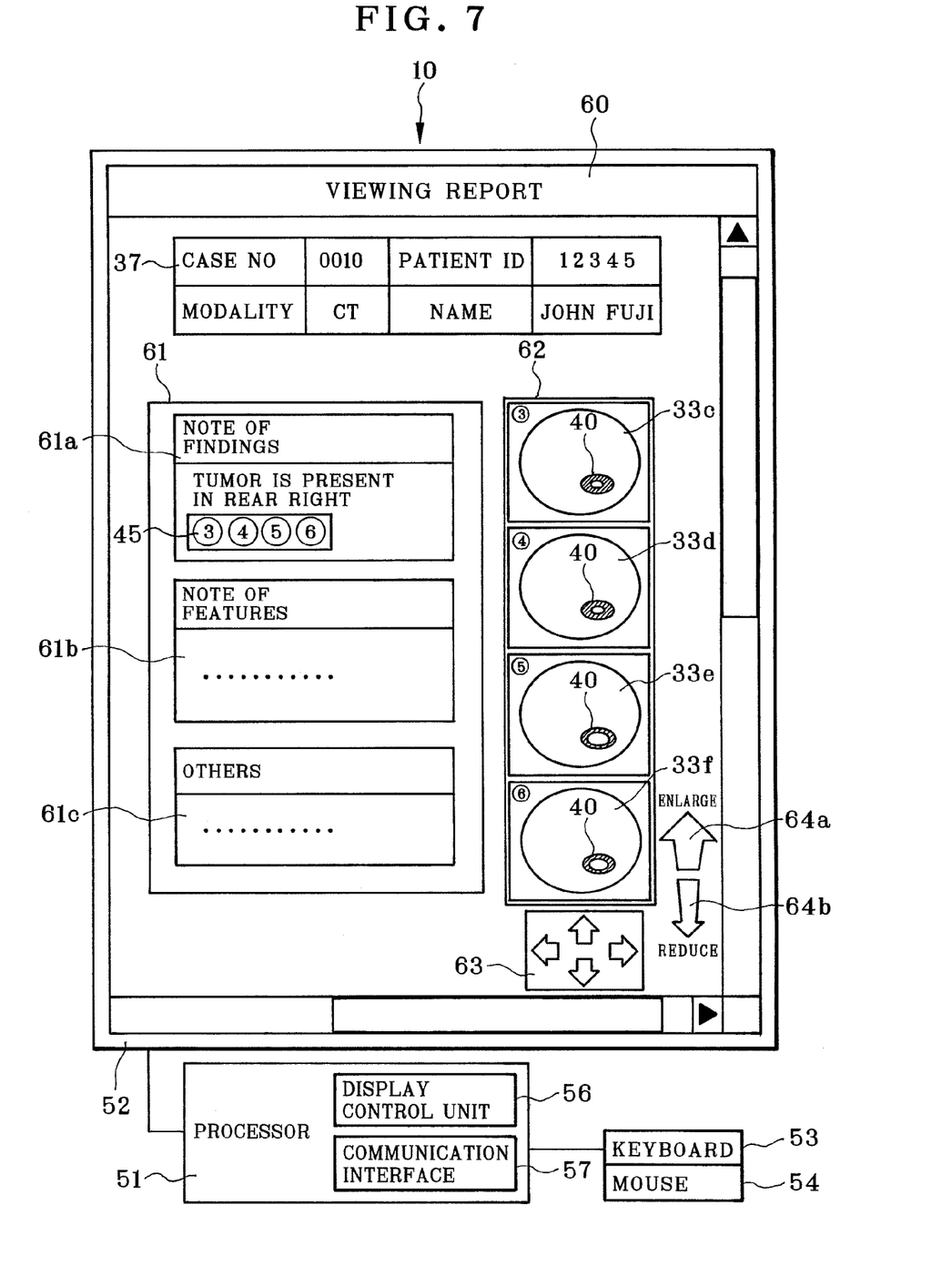
FIG. 7 is a front elevation illustrating a reporting screen area.

In the embodiment, the local terminal device 10 retrieves and displays a medical report, for a doctor to view the report as a result of his or her request for the examination. In FIG. 7, the local terminal device 10 includes a processor 51, a monitor display panel 52 as user interface, a keyboard 53 and a mouse 54. A display control unit 56 and a communication interface 57 are provided in the processor 51. A reporting screen area 60 as user interface is caused to appear on the monitor display panel 52 by the display control unit 56 according to the retrieval of the data file of the medical report.

It is possible in the local terminal device 10 to access the report server 12 through the LAN 14 by inputting the case number (inspection ID) for retrieving a medical report. Group information assigned to the note on the medical report, and location information related to the region of interest (ROI) 40 in medical images according to the group information, are read when the medical report is received. Data of the medical images are retrieved from the report database 17. The monitor display panel 52 is caused to display the reporting screen area 60 as illustrated in FIG. 7 upon receipt of the medical report and medical images. The reporting screen area 60 includes a patient note window 61 for a note or comment, a specific image area 62, a cursor button 63, and enlargement/reduction buttons 64a and 64b. The patient note window 61 includes patient note areas 61a, 61b and 61c for a note or comment drafted on the editing screen area 30. The specific image area 62 displays all medical images according to the group.

The patient note window 61 displays plural notes and Nos. 3-6 to denote the CT images 33c-33f assigned with the text location 45 of the notes. When Nos. 3-6 are clicked, assignment is checked, and the CT images 33c-33f of the group are displayed on the specific image area 62. Those can be verified for their common body part. Also, location information related to the region of interest (ROI) 40 in the CT images 33c-33f is read. The region of interest 40 is displayed in a visually distinct manner from the remaining portions.

Figure 8:
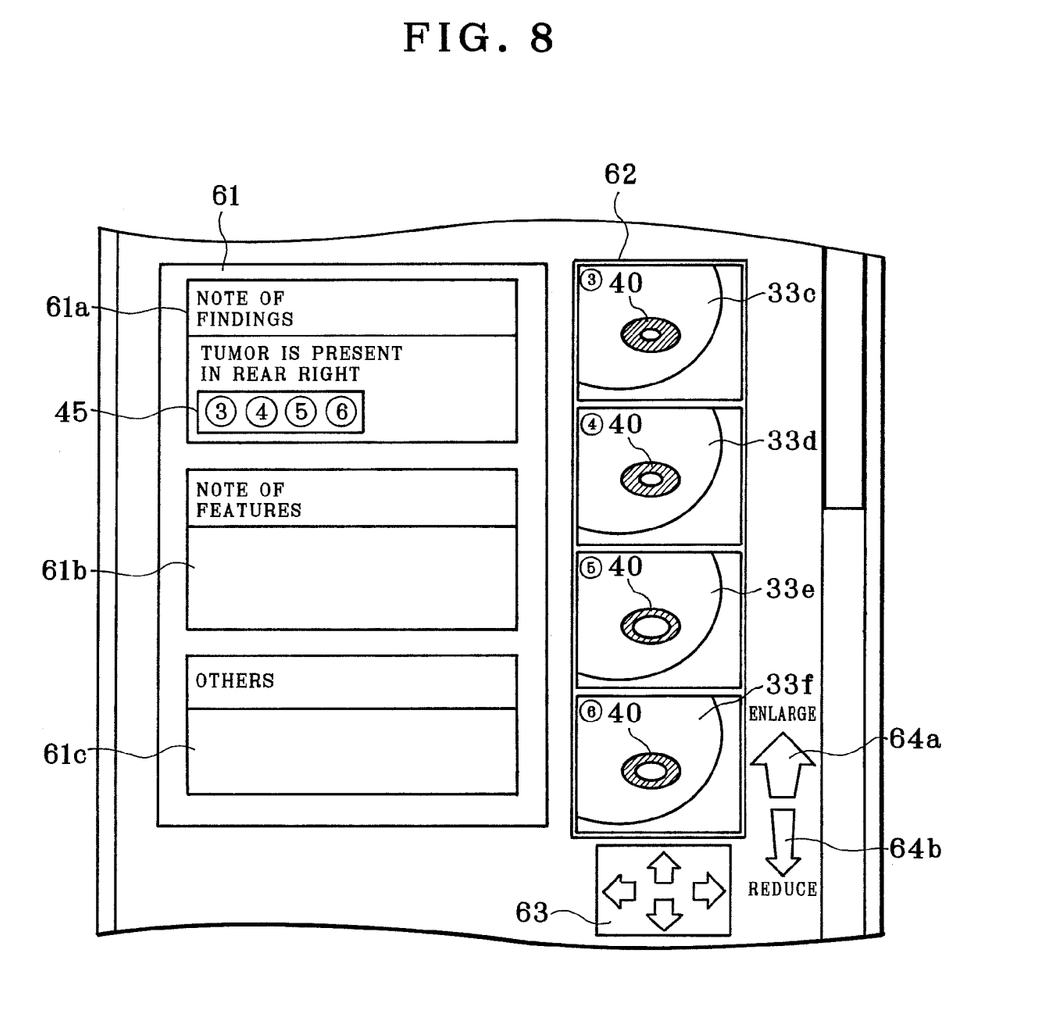
FIG. 8 is a front elevation illustrating the reporting screen area with enlarged CT images of the group.

When the CT images 33c-33f are displayed in the specific image area 62, the cursor button 63 is clicked, to move the images in each of the directions of the cursor button 63 in a scroll manner. Thus, the region of interest (ROI) 40 can be positioned at the center of each of the images. When the enlargement/reduction buttons 64a and 64b are clicked, the images are enlarged or reduced while displayed. The use of the cursor button 63 and the enlargement/reduction buttons 64a and 64b can adjust the region of interest 40 as illustrated in FIG. 8 for the position and size with reference to each of the CT images. Note that all of the CT images 33c-33f in the specific image area 62 can be either enlarged or reduced at the same time, and can be moved in scroll at the same time. Otherwise, it is possible to designate at least one of the images in the specific image area 62 and to enlarge or reduce, or move the designated one of the images.

The operation of the embodiment is described now. The report editing terminal device 13 is operated to edit a medical report in which a text location within the patient note window 36 is assigned to group information and location information of the region of interest (ROI) 40 inside medical images. Information of the medical report is transmitted to the report server 12. When the medical report of the data file is retrieved from the report server 12 and displayed, the location information related to the region of interest 40 in the medical images of the group is assigned to the medical report together with the group information. Thus, all the medical images can be displayed with the region of interest 40 of one patient and in a distinct manner for the region of interest 40. As a doctor after the request for the examination can view all the medical images of the group with the region of interest 40, the medical images are verified for their common body part. The precision in the diagnosis can be high. All the medical images according to the group can be displayed by use of the local terminal device 10 in an enlarged manner about a center defined at the region of interest 40. Thus, the precision in the diagnosis can be still higher by the observation of the enlarged images.

Figure 9:
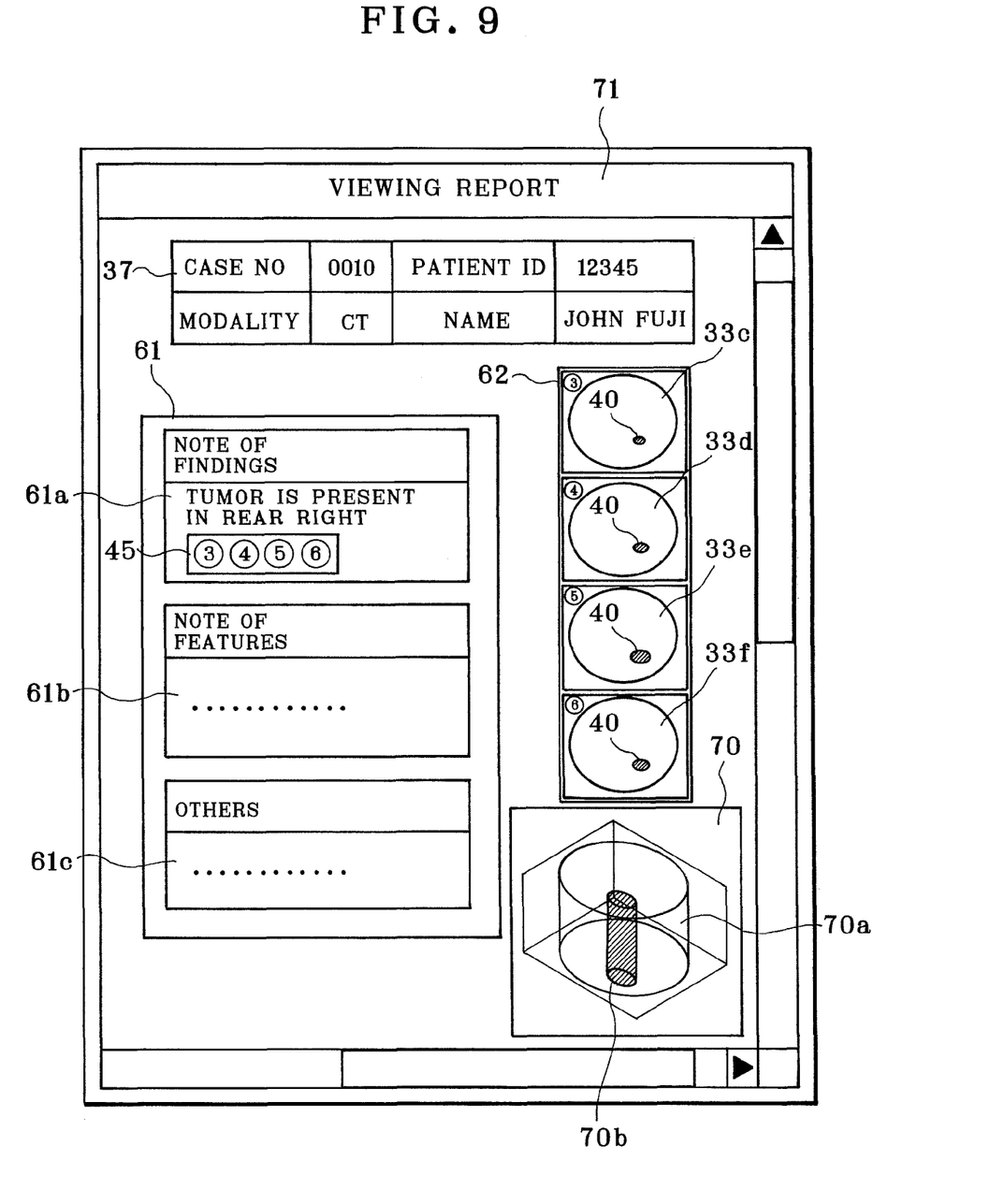
FIG. 9 is a front elevation illustrating another preferred reporting screen area with 3D images.

In the embodiment, medical images are displayed in a two dimensional manner. In contrast, another preferred embodiment of FIG. 9 is based on a display method of three dimensional images by reconstruction of tomographic images obtained by a CT device or MRI device. On a reporting screen area 71 as user interface, a 3D image 70 is displayed. The display control unit 56 in the processor 51 of the local terminal device 10 includes a component for reconstruction of tomographic images to create a 3D image.

To display the 3D image 70 after reconstruction with the CT images 33c-33f as illustrated in FIG. 9, a slice thickness used in the course of forming the CT images 33c-33f is input initially. As a method of inputting the slice thickness, a service console of the local terminal device 10 can be operated. Also, information of the slice thickness can be previously assigned to the CT images 33c-33f, and can be read.

A value of a slice thickness is used to reconstruct the CT images 33c-33f in an overlaid manner on one another to display the CT images 33c-33f on the reporting screen area 71, to create the 3D image 70. It is possible to use an actual value of the slice thickness, or to use a reference thickness as a product obtained by multiplying the slice thickness by a predetermined coefficient. Also for the region of interest (ROI) 40 included in the CT images 33c-33f, images are reconstructed into a 3D image in the same processing. A 3D image portion 70b of the region of interest 40 is displayed and overlapped with a 3D image portion 70a of the entirety of the CT images. The 3D image portion 70b of the region of interest 40 is displayed together with the 3D image portion 70a of the entirety of the CT images for indication of an actual position relation according to the location information of the region of interest 40 assigned to the medical report. The region of interest 40 can be recognized visually in the three dimensional indication, to raise precision in the diagnosis.

In the above embodiment, the notes and medical images are displayed on a common display panel. However, it is possible to use a first display panel for displaying medical images and a second display panel for displaying a note of a medical report and the like.

In the above embodiment, the one text location in the patient note window 36 is assigned to group information and location information related to the region of interest (ROI) 40 of medical images according to the group information. However, plural locations in the patient note window 36 can be designated, and each of the locations in the patient note window 36 can be assigned to group information and location information related to the region of interest 40 of medical images according to the group information.

Also, medical images of the invention may be endoscopic images or the like other than tomographic images. Various well-known techniques in the DICOM (Digital Imaging and Communication in Medicine) in the field of the medical image filing may be used in combination with the present invention.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:
1. A medical reporting system comprising:
a display panel for displaying plural medical images;
a ROI setting unit for designating a region of interest in said medical images;
a group setting unit for setting a group of specific medical images having said region of interest among said plural medical images, to generate group information of said group;
a report editor for displaying a note area for inputting a note related to said specific medical images; and
an assigning unit for assigning a text location of said note area to location information of said region of interest in said specific medical images assigned to said group information, so as to store said text location and said location information.

2. A medical reporting system as defined in claim 1, wherein said ROI setting unit extracts an abnormal shadow from data of said medical images, and said region of interest is a portion with said abnormal shadow.

3. A medical reporting system as defined in claim 1, further comprising:
- a reporting display panel;
- a display control unit for controlling said reporting display panel according to said text location and said location information assigned to said group information, to display said specific medical images, said region of interest and said note.

4. A medical reporting system as defined in claim 3, wherein said display control unit displays said specific medical images according to said group information and said location information.

5. A medical reporting system as defined in claim 3, wherein said display control unit enlarges or reduces said specific medical images simultaneously in said reporting display panel by display control.

6. A medical reporting system as defined in claim 3, wherein said display control unit enlarges or reduces said specific medical images discretely from one another by display control.

7. A medical reporting system as defined in claim 3, wherein said display control unit moves said specific medical images simultaneously in a scroll manner.

8. A medical reporting system as defined in claim 3, wherein said display control unit moves said specific medical images in a scroll manner discretely from one another by display control.

9. A medical reporting system as defined in claim 1, further comprising:
- a first terminal device having said report editor, said ROI setting unit and said group setting unit;
- a second terminal device for communicating with said first terminal device through a network; and
- a reporting display panel, controlled by said second terminal device, for displaying at least said specific medical images and said note.

10. A medical reporting system as defined in claim 1, wherein said plural medical images are tomographic images of a body.

11. A medical reporting system as defined in claim 10, further comprising a processor for combining said tomographic images to reconstruct a 3D image.

12. A medical reporting apparatus comprising:
- a display panel for displaying plural medical images;
- a ROI setting unit for designating a region of interest in said medical images;
- a group setting unit for setting a group of specific medical images having said region of interest among said plural medical images, to generate group information of said group;
- a report editor for displaying a note area for inputting a note related to said specific medical images; and
- an assigning unit for assigning a text location of said note area to location information of said region of interest in said specific medical images assigned to said group information, so as to store said text location and said location information.

13. A medical reporting apparatus as defined in claim 12, wherein said ROI setting unit extracts an abnormal shadow from data of said medical images, and said region of interest is a portion with said abnormal shadow.

14. A medical reporting method comprising:
- a display step of displaying plural medical images;
- a ROI setting step of designating a region of interest in said medical images;
- a group setting step of setting a group of specific medical images having said region of interest among said plural medical images, to generate group information of said group;
- an editing step of displaying a note area for inputting a note related to said specific medical images; and
- an assigning step of assigning a text location of said note area to said group information, and assigning location information of said region of interest in said specific medical images to said group information.

* * * * *